United States Patent
Kim et al.

(10) Patent No.: US 10,378,047 B2
(45) Date of Patent: Aug. 13, 2019

(54) METHOD FOR PREDICTION OF PROGNOSIS BY HUMAN PAPILLOMAVIRUS DNA INTEGRATION PATTERN

(71) Applicant: NATIONAL CANCER CENTER, Goyang-si (KR)

(72) Inventors: Joo-Young Kim, Seoul (KR); Hye-Jin Shin, Seoul (KR); Jung Nam Joo, Goyang-si (KR); Bo Ram Park, Seoul (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 14/991,119

(22) Filed: Jan. 8, 2016

(65) Prior Publication Data
US 2016/0201149 A1 Jul. 14, 2016

(30) Foreign Application Priority Data
Jan. 8, 2015 (KR) .................. 10-2015-0002807

(51) Int. Cl.
*C12Q 1/6841* (2018.01)
(52) U.S. Cl.
CPC ...... *C12Q 1/6841* (2013.01); *C12Q 2600/112* (2013.01); *C12Q 2600/118* (2013.01)
(58) Field of Classification Search
None
See application file for complete search history.

(56) References Cited

U.S. PATENT DOCUMENTS

2004/0248107 A1  12/2004  Sokolova et al.

FOREIGN PATENT DOCUMENTS

KR      20090009073 A      1/2009

OTHER PUBLICATIONS

Shin et al. (2014) Physical Status of Human Papillomavirus Integration in Cervical Cancer is Associated with Treatment Outcome of the Patients Treated with Radiotherapy. PLoS ONE 9(1): e78995. doi:10.1371/journal.pone.0078995.*
Li et al. Correlation between physical status of human papilloma virus and cervical carcinogenesis. J Huazhong Univ Sci Technolog Med Sci. Feb. 2012;32(1):97-102. Epub Jan. 27, 2012.*
Kalantari et al. Conserved methylation patterns of human papillomavirus type 16 DNA in asymptomatic infection and cervical neoplasia. J Virol. Dec. 2004;78(23):12762-72.*
Vernon et al. Association of Human Papillomavirus Type 16 Integration in the E2 Gene With Poor Disease-Free Survival From Cervical Cancer. Int. J. Cancer (Pred. Oncol.): 74, 50-56 (1997) (Year: 1997).*
Peitsaro et al. Integrated Human Papillomavirus Type 16 Is Frequently Found in Cervical Cancer Precursors as Demonstrated by a Novel Quantitative Real-Time PCR Technique. J. Clin. Microbiol. 2002, 40:886-891. (Year: 2002).*
Hong et al. Postoperative Low-Pelvic Irradiation for Stage I-IIA Cervical Cancer Patients With Risk Factors Other Than Pelvic Lymph Node Metastasis. Int. J. Radiation Oncology Biol. Phys., 2002, 53: 1284-1290. (Year: 2002).*
Biewenga et al. Prognostic Model for Survival in Patients With Early Stage Cervical Cancer. Cancer 2011;117:768-76. (Year: 2011).*
Cooper et al., "Episomal and integrated human papillomavirus in cervical neoplasia shown by non-isotopic in situ hybridisation," *Journal of Clinical Pathology* 44(12):990-996, 1991. (8 pages).
Kim et al., "Investigating Molecular Predictive Factors for Radiosensitivity of the Uterine Cervical Cancer," Final Report, Republic of Korea National Cancer Center, Nov. 7, 2011, 50 pages. (with English Summary).
Hudelist et al., "Physical state and expression of HPV DNA in benign and dysplastic cervical tissue: different levels of viral integration are correlated with lesion grade," *Gynecologic Oncology* 92:873-880 (2004).
Kim et al., "Low Initial Human Papilloma Viral Load Implicates Worse Prognosis in Patients with Uterine Cervical Cancer Treated With Radiotherapy," *Journal of Clinical Oncology* 27(30):5088-5093 (Oct. 20, 2009).
Peitsaro et al., "Integrated Human Papillomavirus Type 16 is Frequently Found in Cervical Cancer Precursors as Demonstrated by a Novel Quantitative Real-Time PCR Technique," *Journal of Clinical Microbiology* 40(3):886-891 (Mar. 2002).
Shin et al., "Physical Status of Human Papillomavirus Integration in Cervical Cancer is Associated with Treatment Outcome of the Patients Treated with Radiotherapy," *PLoS One* 9(1):e78995 (8 pages) (Jan. 2014).

(Continued)

*Primary Examiner* — Nianxiang Zou
(74) *Attorney, Agent, or Firm* — Seed Intellectual Property Law Group LLP

(57) ABSTRACT

Provided is a method for analyzing the prognosis of cervical cancer according to the human papillomavirus (HPV) DNA integration pattern. The method of analyzing the prognosis of cervical cancer according to the human papillomavirus DNA integration pattern of the present invention enables an observation of the HPV DNA integration pattern with accuracy and convenience via in situ hybridization (ISH) compared to qPCR analysis. Since the prognosis of cervical cancer having the tumors with an episomal pattern and an integrated pattern can be significantly distinguished when the HPV DNA integration patterns are classified by the above method, the survival rate after radiotherapy of cervical cancer, and in particular invasive cervical cancer, can be more accurately analyzed.

3 Claims, 12 Drawing Sheets
Specification includes a Sequence Listing.

(56) References Cited

OTHER PUBLICATIONS

The 19$^{th}$ Japan—Korea Cancer Research Workshop, *"Current Perspectives on Gynecologic Cancer and Emerging Cancer Diagnosis Methods,"* Nov. 28-30, 2014 Hyatt Regency Jeju, Korea (13 pages).

* cited by examiner

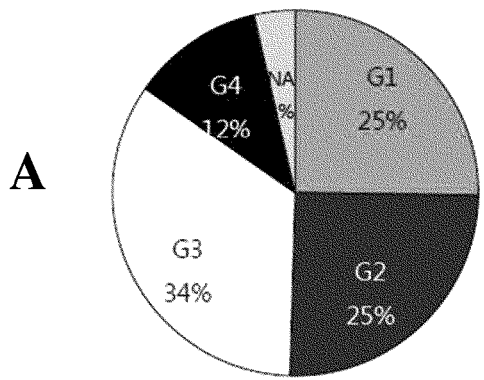
A
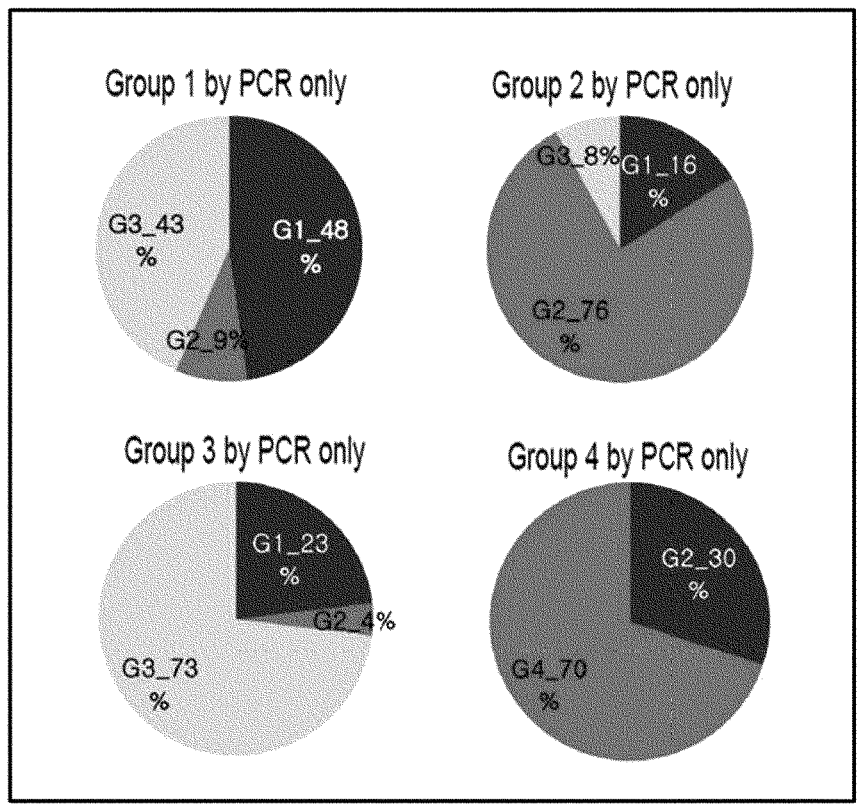
B
FIG. 7

Development Set

| Risk Group | | Estimated 1 year survival | Estimated 2 year survival | No. of Patients(%) | Event(%) | Disease Free Survival HR (95% CI) | p-value | Disease Free Survival (linear trend) HR (95% CI) | p-value |
|---|---|---|---|---|---|---|---|---|---|
| Good | : xbeta < mean-std | 1.0000 | 1.0000 | 11 (13.25) | 0 (0) | | | 2.84 (1.74-4.66) | <.0001 |
| Fairly good | : xbeta < mean | 0.9403 | 0.8796 | 34 (40.96) | 4 (11.76) | 1 (ref) | | | |
| Fairly poor | : xbeta < mean+std | 0.8500 | 0.7500 | 20 (24.1) | 7 (35) | 3.33 (0.97-11.4) | 0.0552 | | |
| Poor | : xbeta > mean+std | 0.6111 | 0.4444 | 18 (21.69) | 12 (66.67) | 7.24 (2.32-22.57) | 0.0006 | | |

| Group by Integration pattern | Risk group | | | | |
|---|---|---|---|---|---|
| | Good | Fairly good | Fairly poor | Poor | Total |
| A | 11 (64.71) | 6 (35.29) | 0 (0) | 0 (0) | 17 |
| B | 0 (0) | 28 (42.42) | 20 (30.3) | 18 (27.27) | 66 |
| Total | 11 | 34 | 20 | 18 | 83 |

FIG. 10

Validation Set

| Risk Group | | Estimated 1 year survival | Estimated 2 year survival | No. of Patients(%) | Event(%) | Disease Free Survival HR (95% CI) | p-value | Disease Free Survival (linear trend) HR (95% CI) | p-value |
|---|---|---|---|---|---|---|---|---|---|
| Good | : xbeta < mean-std | 0.9215 | 0.9215 | 27 (13.17) | 3 (11.11) | 1 (ref) | | 1.69 (1.27-2.25) | 0.0003 |
| Fairly good | : xbeta < mean | 0.7941 | 0.7676 | 40 (19.51) | 10 (25) | 2.44 (0.67-8.86) | 0.1754 | | |
| Fairly poor | : xbeta < mean+std | 0.8695 | 0.8183 | 63 (30.73) | 16 (25.4) | 2.45 (0.71-8.39) | 0.1549 | | |
| Poor | : xbeta > mean+std | 0.6248 | 0.5812 | 75 (36.59) | 34 (45.33) | 5.54 (1.7-18.05) | 0.0045 | | |

| Group by Integration pattern | Risk group | | | | |
|---|---|---|---|---|---|
| | Good | Fairly good | Fairly poor | Poor | Total |
| A | 27 (72.97) | 6 (16.22) | 4 (10.81) | 0 (0) | 37 |
| B | 0 (0) | 34 (20.24) | 59 (35.12) | 75 (44.64) | 168 |
| Total | 27 | 40 | 63 | 75 | 205 |

FIG. 11

| Total population | | | | | | | | | |
|---|---|---|---|---|---|---|---|---|---|
| Risk Group | | Estimated 1 year survival | Estimated 2 year survival | No. of Patients(%) | Event(%) | Disease Free Survival | | Disease Free Survival (linear trend) | |
| | | | | | | HR (95% CI) | p-value | HR (95% CI) | p-value |
| Good | : xbeta < mean-std | 0.9256 | 0.9256 | 42 (14.58) | 4 (9.52) | 1 (ref) | | 2.12 (1.65-2.72) | <.0001 |
| Fairly good | : xbeta < mean | 0.8697 | 0.8185 | 101 (35.07) | 21 (20.79) | 2.33 (0.8-6.79) | 0.1209 | | |
| Fairly poor | : xbeta < mean+std | 0.7965 | 0.7410 | 96 (33.33) | 32 (33.33) | 4.06 (1.44-11.47) | 0.0083 | | |
| Poor | : xbeta > mean+std | 0.5296 | 0.4350 | 49 (17.01) | 29 (59.18) | 10.22 (3.58-29.15) | <.0001 | | |

| Group by Integration pattern | Risk group | | | | |
|---|---|---|---|---|---|
| | Good | Fairly good | Fairly poor | Poor | Total |
| A | 42 (77.78) | 6 (11.11) | 6 (11.11) | 0 (0) | 54 |
| B | 0 (0) | 95 (40.6) | 90 (38.46) | 49 (20.94) | 234 |
| Total | 42 | 101 | 96 | 49 | 288 |

FIG. 14

METHOD FOR PREDICTION OF PROGNOSIS BY HUMAN PAPILLOMAVIRUS DNA INTEGRATION PATTERN

CROSS-REFERENCE TO RELATED APPLICATIONS

This U.S. non-provisional patent application claims priority under 35 U.S.C. § 119 of Korean Patent Application No. 10-2015-0002807, filed on Jan. 8, 2015, the entire contents of which are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690196_402_SEQUENCE_LISTING.txt. The text file is 3.6 KB, was created on Jan. 7, 2016, and is being submitted electronically via EFS-Web.

BACKGROUND OF THE INVENTION

The present invention disclosed herein relates to a method of analyzing the prognosis of cervical cancer according to human papillomavirus (HPV) DNA integration pattern, and more particularly, to a method of observing the pattern of the DNA of high risk-human papillomavirus (HR HPV), which is present in cervical cancer tissues, being inserted into human cervical cancer cells by in situ hybridization (ISH), and then analyzing the prognosis of a patient after radiotherapy according to the integrated pattern of the HPV DNA.

Human papillomavirus (HPV) in high risk group induces invasive cervical cancer while causing a persistent infection in human cervical cancer tissues over a span of a few years to a few tens of years. According to the Korean cancer registration statistics data in data, although the frequency of invasive cervical cancer is reduced from 19.3 to 10, frequency of cervical intraepithelial neoplasia, which is considered as a previous stage of invasive cervical cancer, is increased to 19 per hundred thousand people in 2010 from 7.5 per hundred thousand people in 1993. This implies that the gynecological cancer associated with the infection of the human papillomavirus in high risk group still remains as an important issue with respect to the incidence of gynecological cancer. According to the recent Korean cancer registration statistics, there are about 3700 to 3800 new cancer patients each year, and they are being treated using surgical operations, radiations, anticancer agents, etc., either alone or in combination. For cancers in clinical stage 1, surgical operations are performed mostly. However, when the tumor size is big or there is a lymph node metastasis, or for cancers in clinical stage 2, radiotherapy becomes the major therapy. In Korea, the five-year survival rate in cervical cancer patients is about 80%, being relatively higher than those of other countries. However, the death rate due to cervical cancer is still ranked third worldwide.

In general, human papillomavirus-related cancer species are sensitive to radiations and thus can be treated well by radiotherapy but the adverse effects of radiotherapy have a room for improvement. Additionally, since this disease is well treated by radiotherapy, the reduction in the levels of radiation and anticancer agents, which were typically used in the past to a particular group of patients, may improve the quality of patients' lives while capable of increasing the rate of complete cure.

Instead of the current uniform therapies, the development of a therapeutic method which includes classifying the patients into a low risk group and a high risk group, and applying a lesser amount of radiation and a minimal amount of anticancer agents for patients in the low risk group, whereas applying a treatment for improving the complete cure rate for patients in the high risk group, will enable the increase of complete cure rate of cervical cancer worldwide and the improvement in the quality of cervical cancer patients' lives than what they enjoy at present.

In the typical technologies, US Patent Application Publication No. 2004-0248107 discloses probe sets for the detection of high grade dysplasia and carcinoma in cervical cells, and a method for detecting HPV infected cells using ISH method, and Gernot Hudelist et al. disclose a method for observing the physical patterns of HPV DNA (episomal, mixed and integrated form) according to the stages of cervical cancer (CIS, CIN1, CIN2, and CIN3) by polymerase chain reaction (PCR) (*Gynecologic Oncology*, 92: 873, 2004). However, these typical methods of analysis involve detecting the tissues where the high risk HPV is present, and then examining the presence of pre-invasive cancer (cervical intraepithelial neoplasm (CIN I, CIN II)), where HPV has been analyzed to be infected or integrated only in an episomal form; and in situ cancer (CIN III) and invasive cancer, where HPV has been analyzed to be present in an integrated form, and thus simply provide a method of distinction whether it will be progressed into a cancer or it is a pre-cancerous lesion, and these methods had a limitation in that it cannot provide a clear distinction from stage IV to stage IVB of locally advanced cervical cancer.

Meanwhile, in the previous studies, the present inventors had classified the cervical cancer patients into four groups according to the results of real-time qPCR performed using probes and primers specific to E2 hinge region and E6 ORF, and had reported that the integrated HPV DNA pattern was associated with the results of therapeutic treatment of cervical cancer patients by radiation (Shin, H. J. et al., *PLoS One*, 9:e78995, 2014).

However, the determination of the HPV DNA integration pattern and presence of HPV infection by PCR alone lacks in accuracy of distinction between the tumor tissues having an episomal form and those having multicopy tandem-repetition integrated HPV. Additionally, there is a limitation in that when the episomal form and other integration patterns are co-present in the same tissue, it is difficult to figure out the presence ratio of each form and observe the integration form of HPV DNA according to the location within the tumor tissue.

Under these circumstances, the present inventors have made intensive efforts to develop a method for an accurate and convenient analysis of the prognosis of invasive cervical cancer through observation of the HPV DNA integration pattern within the cervical cancer, and as a result, they have discovered that the prognosis of patients after radiotherapy can be effectively analyzed according to the DNA integration pattern, by observing the pattern of HPV DNA integrated in the cervical cancer cells using in situ hybridization (ISH) method, and also confirmed that when the HPV DNA integration patterns were classified by the above method, the prognosis of cervical cancer patients having the episomal pattern and the integrated pattern was clearly distinguishable, thereby completing the present invention.

SUMMARY OF THE INVENTION

An object of the present invention is to provide a method of analyzing the prognosis of cervical cancer by observation of human papillomavirus DNA integration patterns.

Additionally, another significance that can be clinically obtained by the present invention is to provide a method for individualizing the cervical cancer treatment, which includes classifying the cervical cancer patients according to the human papillomavirus DNA integration patterns, and performing appropriate radiation and/or use of anticancer agents according to the episomal pattern and the integrated pattern.

In order to resolve the first object, the present invention provides a method for analyzing the prognosis of cervical cancer including: obtaining tumor tissues from cervical cancer patients and observing the of human papillomavirus DNA integration pattern by in situ hybridization (ISH); and analyzing the prognosis of cervical cancer according to the human papillomavirus DNA integration pattern.

In a preferred embodiment of the present invention, the human papillomavirus DNA integration pattern may be classified into: group 1, which comprises an episomal form; group 2, which has a single-copy integration pattern without an episomal form; group 3, which comprises a multicopy tandem-repetition integrated pattern; and group 4, in which the human papillomavirus DNA integration pattern is not observed.

In another preferred embodiment of the present invention, the cervical cancer patients may be classified, according to the human papillomavirus DNA integration pattern, into: group A patients exhibiting episome pattern frequency of 80% to 100%; group B, in which the single-copy integration pattern or the multicopy tandem-repetition integrated pattern are observed, or the human papillomavirus DNA integration pattern is not observed in the patients.

In still another preferred embodiment of the present invention, group B may have a hazard ratio of 1.4 to 7.44 when the hazard ratio regarding the survival rate of group A is set at 1.

In still another preferred embodiment of the present invention, the hazard ratio may be measured using a multivariable cox proportional hazards model, which is drawn to enable the analysis of a radiotherapy result according to the human papillomavirus DNA integration pattern.

In still another preferred embodiment of the present invention, the patient groups, in the method of analyzing the prognosis of cervical cancer, may be classified into four risk groups from the low risk group (good) to the high risk group (poor) (good-fairly good-fairly poor-poor), according to the survival rates analyzed from the multivariable cox proportional hazards model.

In still another preferred embodiment of the present invention, the survival rate of the lowest risk group (good) after radiotherapy for 2 years may be from 90% to 95%, that of the second lowest risk group (fairly good) after radiotherapy for 2 years may be 80% to 85%, that of the second highest risk group (fairly poor) after radiotherapy for 2 years may be 70% to 75%, and that of the highest risk group (poor) after radiotherapy for 2 years may be 40% to 45%.

In still another preferred embodiment of the present invention, the cervical cancer may be invasive cervical cancer, and the locally progressed invasive cervical cancer at a stage of IB to IVB.

In order to resolve the second object, the present invention provides, as a method for analyzing the prognosis of cervical cancer including, a method of individualizing the cervical cancer treatment including: classifying cervical cancer patients according to the human papillomavirus DNA integration pattern and analyzing the prognosis; and performing the use of an appropriate radiation and/or an anti-cancer agent according to the analysis; or a method for monitoring the cervical cancer treatment.

Advantageous Effects of the Invention

The method of analyzing the prognosis of cervical cancer according to the human papillomavirus (HPV) DNA integration pattern of the present invention enables an observation of the HPV DNA integration pattern with accuracy and convenience via in situ hybridization (ISH) compared to that of qPCR analysis. Since the prognosis of cervical cancer having the tumors with an episomal pattern and an integrated pattern can be significantly distinguished when the HPV DNA integration patterns are classified by the above method, the survival rate after radiotherapy of cervical cancer, and in particular invasive cervical cancer, can be more accurately analyzed.

Additionally, according to the HPV DNA integration patterns, the cervical cancer patients having an episomal pattern will have good prognosis, and thus they can reduce complications due to therapies while maintaining the rate of complete cure by minimizing the use of radiation or anti-cancer agents. In contrast, in the case of the cervical cancer patients, who mainly have the integration pattern instead of the episomal pattern, they can improve the their life quality while increasing the rate of complete cure by applying a more strengthened therapy to improve complete cure rate.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 7 shows the data illustrating the classification of human papillomavirus DNA integration patterns according to qPCR method and ISH method, in which (A) shows the data illustrating distribution of each group classified by qPCR method with respect to 80 cervical cancer patients, and (B) shows the data illustrating the distribution of the number of patients with a group shift when observed through the ISH method per each group according to the result of qPCR;

FIG. 10 shows the data illustrating the hazard ratio (HR) of the disease-free survival rate of the four risk groups classified according to the survival rate analyzed in the development set, and the patient groups classified by the human papillomavirus DNA integration pattern that belongs to each risk group;

FIG. 11 shows the data illustrating the hazard ratio (HR) of the disease-free survival rate of the four risk groups classified according to the survival rate analyzed in the validation set, and the patient groups classified by the human papillomavirus DNA integration pattern that belongs to each risk group;

FIG. 14 shows the data illustrating the hazard ratio (HR) of the disease-free survival rate of each of the risk groups classified according to the survival rate analyzed in the entire population group, and the patient groups classified by the human papillomavirus DNA integration pattern that belongs to each risk group.

DETAILED DESCRIPTION OF PREFERRED EMBODIMENTS

Figure 1:
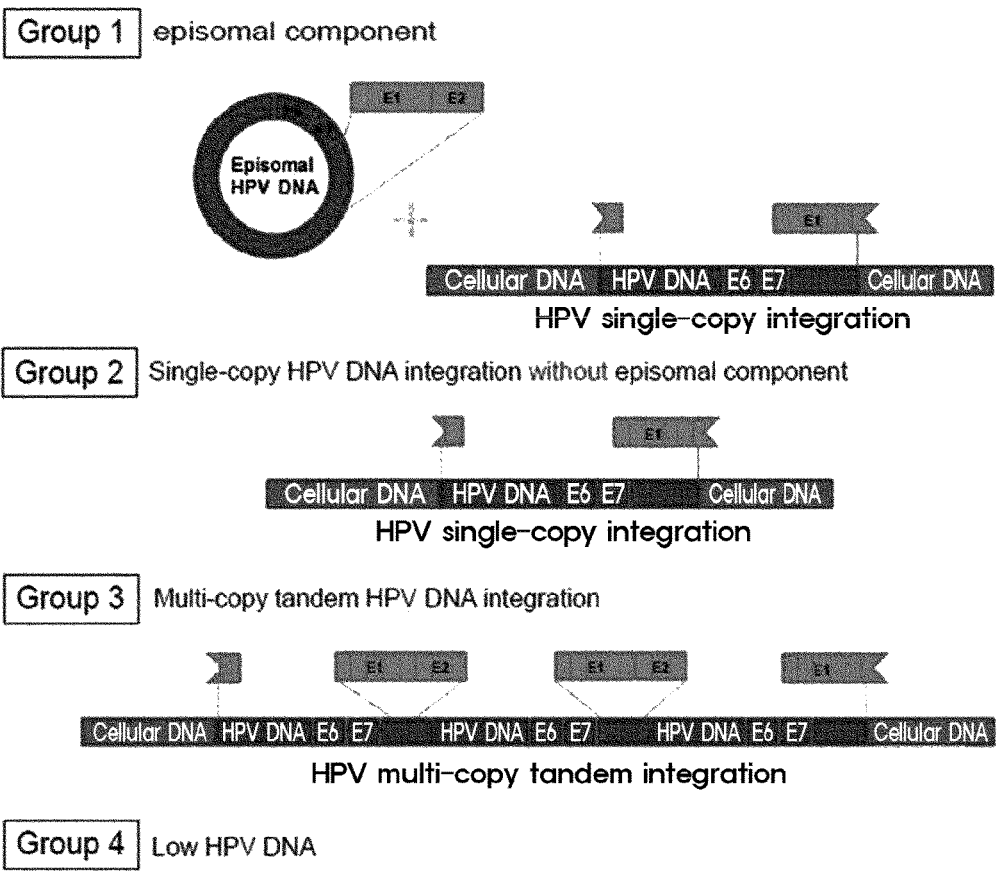
FIG. 1 is a schematic diagram illustrating the classification according to human papillomavirus DNA integration patterns.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

The present invention will be described in more details herein below.

As described above, although methods for observing physical forms of HPV DNA according to the stages (CIS, CIN1, CIN 2, and CIN3) of cervical cancer were studied using the typical method of polymerase chain reaction (PCR), the determination of HPV DNA integration patterns and the presence of HPV infection based on PCR alone was difficult to distinguish from the tissues having various other integration patterns along with the episomal pattern, and in particular, there was a limitation in that the accuracy of distinguishing the tumors mainly having an episomal pattern from the those having HPV with a multicopy tandem-repetition integrated pattern was poor.

The present invention has attempted to resolve the above-mentioned limitations by providing a method for analyzing the prognosis of cervical cancer according to human papillomavirus DNA integration patterns. As such, when the patterns of the HPV DNA integrated in cervical cancer cells are observed using in situ hybridization (ISH) method, the prognosis of the cervical cancer patients after radiotherapy can be effectively analyzed according to the integration form of viral DNA.

Accordingly, the present invention relates to a method for analyzing the prognosis of cervical cancer including obtaining tumor tissues from cervical cancer patients and observing the of human papillomavirus DNA integration pattern by in situ hybridization (ISH); and analyzing the prognosis of cervical cancer according to the human papillomavirus DNA integration pattern.

As used herein, the term "in situ hybridization" refers to a process of detecting DNA or RNA and hybrid-formation without extracting intracellular DNA or RNA in detecting fragments of target DNA or RNA, in which "in situ" means "situated in its original position" and may be divided into three different kinds. First, in situ hybridization aims at selecting a phage or plasmid library, which is a hybrid formation achieved by adsorbing DNA of a phage plaque or *E. coli* colony on an agar medium to a filter. Second, in situ hybridization aims at determining the gene location on a chromosome, which is a hybrid formation with chromosomal DNA. Third, in situ hybridization aims at identifying the cells in which a target gene is expressed in tissue sections and cultured cells, which is mainly a hybrid formation with mRNA.

The cervical cancer, whose prognosis can be analyzed by the method of the present invention, may be preferably invasive cervical cancer, and more preferably, the prognosis of stages from IB to IVB of invasive cervical cancer, which are progressed stages of invasive cervical cancer.

The present inventors, as a result of real-time qPCR using probes and primers specific to E2 hinge region and E6 ORF performed in previous studies, divided the patients into four groups according to the integration patterns of the HPV DNA, and reported that the integration patterns of the HPV DNA are related to the treatment result of the cervical cancer patients who received radiotherapy (Shin, H. J. et al., *PLoS One*, 9:e78995, 2014).

In the above study, the present inventors have confirmed that the HPV DNA integration pattern is an important factor in determining the prognosis of cervical cancer, and thus, in the present invention, they observed the forms of the integration patterns of the HPV DNA in the cervical cancer cells via in situ hybridization (ISH) method, in order to analyze the prognosis of invasive cervical cancer by the observation of HPV DNA integration patterns in cervical cancer cells with improved accuracy and convenience.

FIG. 1 is a schematic diagram illustrating the classification according to human papillomavirus DNA integration patterns, and according to the human papillomavirus DNA integration patterns, the human papillomavirus DNA integration pattern may be classified into: group 1, which includes an episomal form; group 2, which has a single-copy integration pattern without an episomal form; group 3, which has a multicopy tandem-repetition integrated pattern;

and group 4, in which the human papillomavirus DNA integration pattern is not observed.

The multicopy tandem-repetition integrated pattern of group 3 refers to a form, in which human papillomavirus DNA is tandemly connected and repeatedly integrated within the chromosome of a host cell (a human cervical cancer cell), as shown in FIG. 1.

Figure 2:
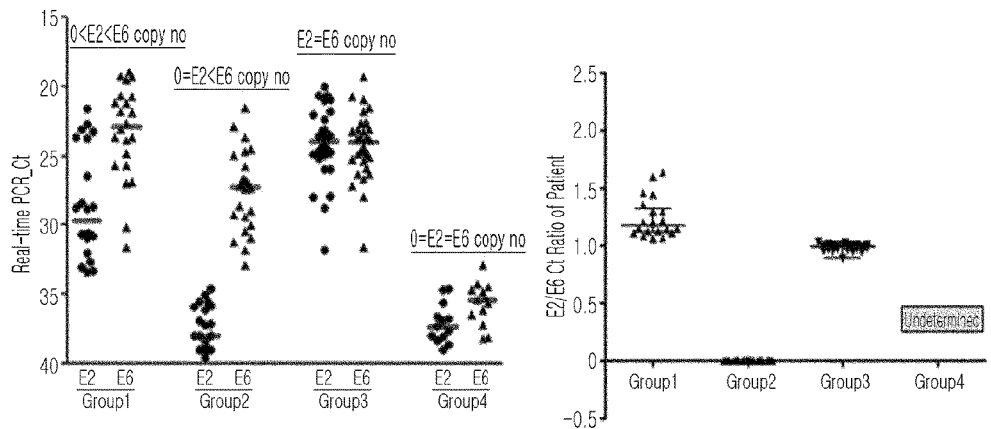
FIG. 2 shows the data illustrating the human papillomavirus DNA integration patterns according to the result of quantitative real-time PCR.

FIG. 2 shows the data illustrating the human papillomavirus DNA integration patterns according to the result of quantitative real-time PCR in the previous study performed by the present inventors. When HPV DNA is integrated into the chromosome of a host cell, it penetrates thereinto while destroying mainly E2 gene. Therefore, the thus-destroyed E2 gene is detected of its copy number using primers and probes which were designed to avoid PCR amplification.

By comparison of the relative copy numbers of E2 and E6 based on this principle, the patients were divided into the following four groups: a single-copy integration including an episomal factor (group 1); a single-copy integration without an episomal factor (group 2); a multicopy tandem-repetition integrated pattern (group 3); and a low HPV (group 4). Regarding group 1, a lower copy number of E2 than that of E6 was detected but it was postulated that the episome patterns and the single-copy integration pattern were mixed because both E2 and E6 showed amplification features. Regarding group 2, it was postulated that the single-copy integration pattern was achieved in both because E2 amplification was not observed. Regarding group 3, it was postulated that they have multicopy a tandem-repetition integrated pattern because the levels of E2 and E6 were shown to be equal.

In an exemplary embodiment of the present invention, human papillomavirus DNA integration patterns were observed by observing the tissues isolated from a cervical cancer patient via in situ hybridization ("ISH", hereinafter) method.

The human papillomavirus DNA integration patterns according to the ISH method may be observed regarding the stained cervical cancer tissues using a microscope, or may be confirmed using a computer-based image analysis program.

Figure 3:
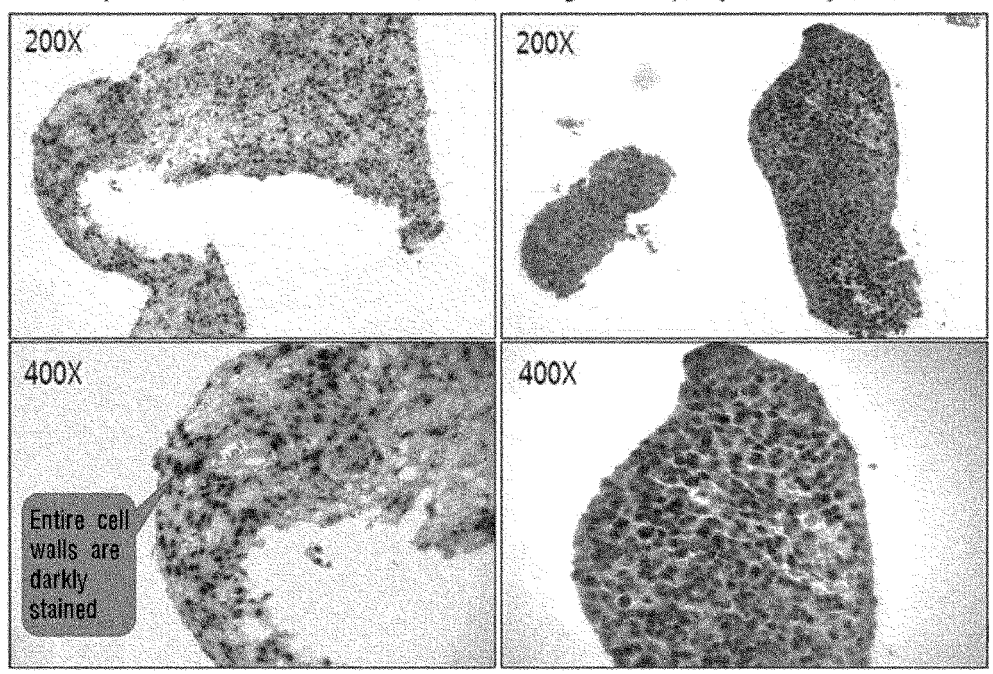
FIG. 3 shows pictures illustrating human papillomavirus DNA integration patterns observed according to the in situ hybridization (ISH) method; group 1 which includes the episomal form (the entire cell nuclei are darkly stained).
Figure 4:
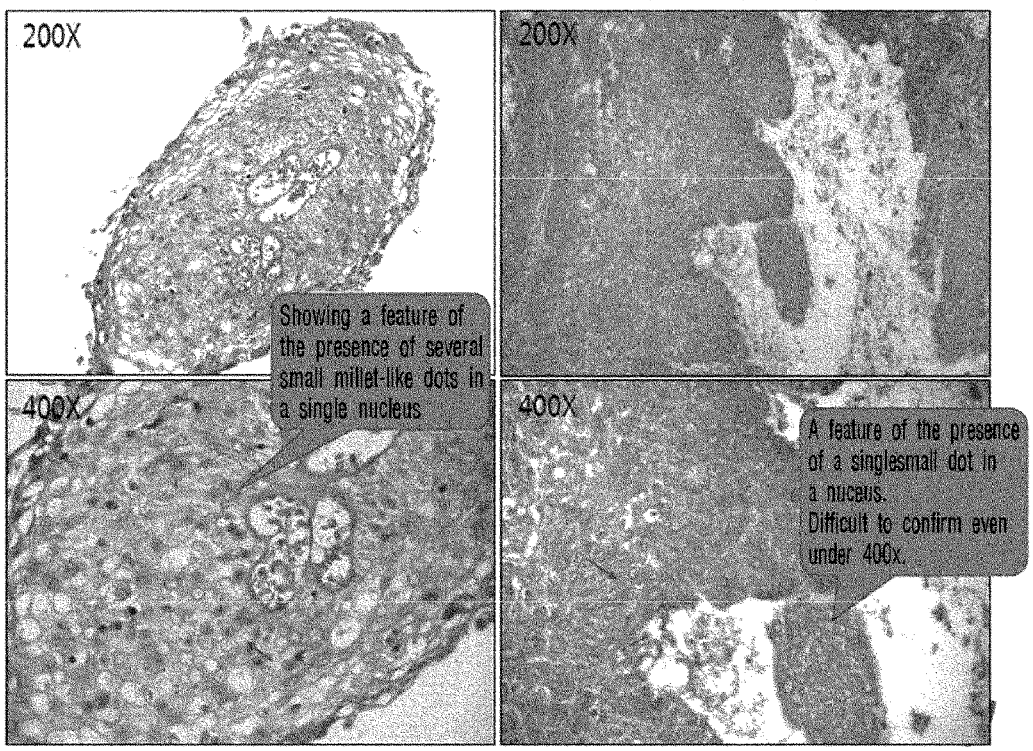
FIG. 4 shows pictures illustrating human papillomavirus DNA integration patterns observed according to the in situ hybridization (ISH) method; group 2 which has a single-copy integration pattern without including an episomal form (one or several small millet-like dots tend to appear inside of each nucleus but they are vaguely observed).
Figure 5:
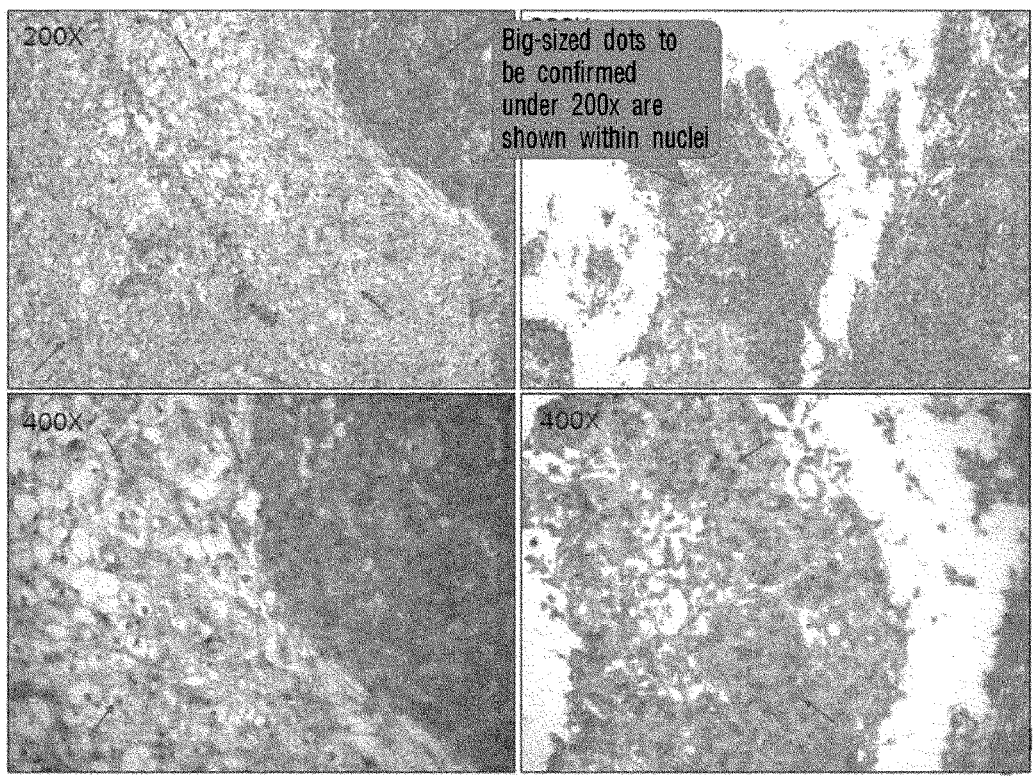
FIG. 5 shows pictures illustrating human papillomavirus DNA integration patterns observed according to the in situ hybridization (ISH) method; group 3 which includes a multicopy tandem-repetition integrated pattern (big-sized dots are observed inside of each nucleus)
Figure 6:
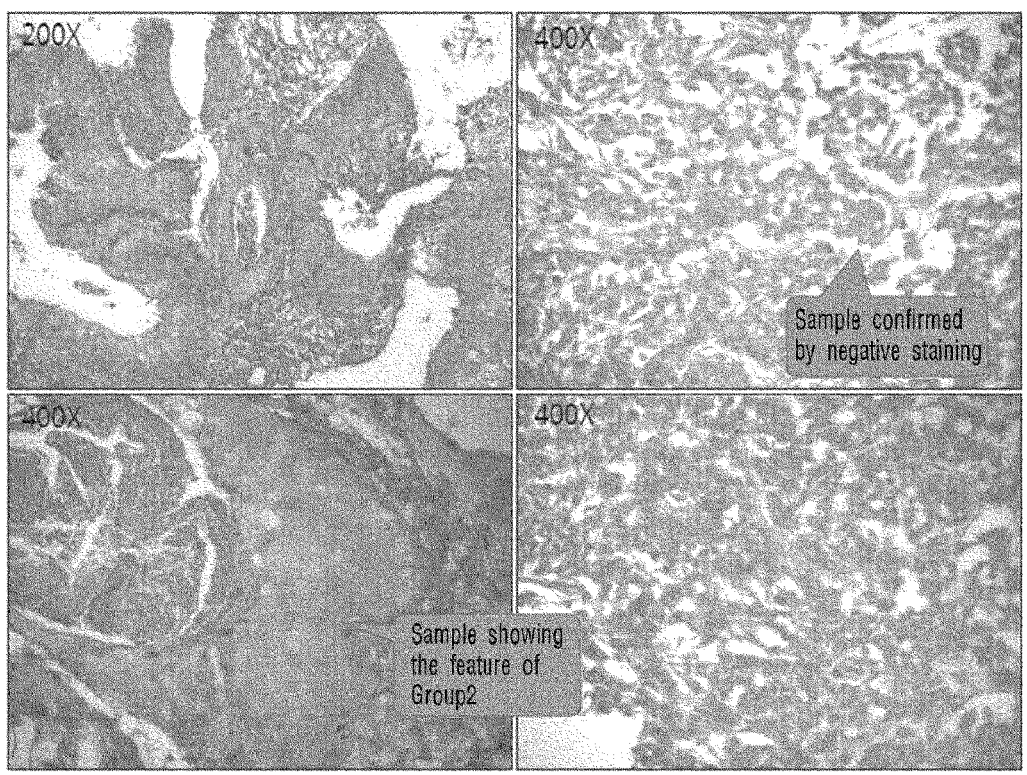
FIG. 6 shows pictures illustrating human papillomavirus DNA integration patterns observed according to the in situ hybridization (ISH) method; group 4, in which the human papillomavirus DNA integration pattern is not observed.

FIGS. 3 to 6 show the pictures observed regarding the human papillomavirus DNA integration patterns according to the ISH method, and unlike what was expected from the PCR result, numerous patient groups showing high-frequency of the episomal pattern in invasive tumor tissues were observed and they were classified into group 1. The episomal pattern of group 1 was shown to be darkly stained over the entire nuclei of the cells as shown in the ISH result (FIG. 3). Group 2, which has the single-copy integration pattern in most tumor tissues, showed the features that either one to several millet-like small dots were present within a single nucleus or vaguely observed (FIG. 4). Group 3, which has a multicopy tandem-repetition integrated pattern, was shown to have big-sized dots within nuclei (FIG. 5), and in group 4, it was confirmed that the human papillomavirus DNA integration pattern was not observed (FIG. 6).

In another exemplary embodiment of the present invention, for the accurate comparison of the analysis of human papillomavirus DNA integration patterns according to ISH method and qPCR, tumor tissues were isolated from 80 cervical cancer patients and the human papillomavirus DNA integration patterns were observed via ISH method and qPCR method, and they were classified into 4 groups according to the observation results.

FIG. 7 shows the data illustrating the classification of human papillomavirus DNA integration patterns according to qPCR method and ISH method. As shown in FIG. 7A, when the 80 cervical cancer patients were classified according to the human papillomavirus DNA integration patterns, it was confirmed that groups 1 to 4 had the ratio of 25%, 25%, 34%, and 12%, respectively.

FIG. 7B shows the data illustrating the distribution of a group shift according to the ISH result of each group in the groups classified according to the qPCR result, and it was confirmed that there was a big difference between PCR method and ISH method. In particular, when the patient group corresponding to group 1 classified by PCR method was reclassified by ISH method, 48% of the patients still remained in group 1, whereas 9% was shifted to group 2 and 43% shifted to group 3. When the patient group corresponding to group 3 classified by PCR method was reclassified by ISH method, 23% of the patients was shifted to group 1 and 4% shifted to group 2, whereas 73% still remained in group 3.

That is, among the patient group classified into group 1 by the PCR result, 43% of the patients belong to group 3 by ISH result, whereas among the patient group classified into group 3 by the PCR result, as many as 23% of the patients belong to group 1 by ISH result. As a result, it was confirmed that PCR result alone cannot provide an accurate distinction between the tumor tissues having an episomal form (group 1) and those having a multicopy tandem-repetition integrated pattern (group 3).

Additionally, through the result observed by ISH method, there were in fact numerous cases when both episomal pattern and the integrated pattern were mixed, and thus it was thought to be necessary to determine the mixed ratio by microscopic observation and, based on the mixed ratio, determine a cut-off point that may significantly affect the treatment prognosis. In this regard, the efficiency and appropriateness of ISH method compared to qPCR method in classification of patient groups according to the HPV DNA integration patterns were confirmed, and in the present invention, for group 1 including the episomal factor, the cut-off point was set at 80% to 100% (tissues having the frequency of episome pattern of 80% or higher) and classified group 1 as such.

Additionally, since ISH method can provide comparative observation of the tumor tissue regions of cervical cancer and HPV DNA integration patterns, it was possible to distinguish the presence of the episomal pattern in invasive tumor tissue regions.

In the present invention, in the case when the cells having an episomal pattern and those having a pattern integrated into the chromosome of a host cell are mixed, it has been attempted to digitize the frequencies accounted for by them based on the ISH experimental results, and more accurately classify the groups according to the human papillomavirus DNA integration patterns, thereby providing an appropriate criteria for determining treatment prognosis.

In an exemplary embodiment of the present invention, for the establishment of a model capable of analyzing the prognosis of cervical cancer patients based on the ISH experimental results of the analysis of the human papillomavirus DNA integration patterns, tumor tissues of 288 constitute cervical cancer patients who received curative radiotherapies with or without in combination with a chemotherapy in the National Cancer Center (Korea), and among them, the samples from 83 patients were used as a development set for the establishment of a model and those from 205 patients were used as a validation set.

In the present invention, according to the human papillomavirus DNA integration patterns, the cervical cancer patients may be classified into group A, in which the frequency of the episome pattern accounted for 80% to 100%; and group B, in which a single-copy integration pattern or a multicopy tandem-repetition integrated pattern were observed or the human papillomavirus DNA integration pattern was not observed.

As shown in Table 2, for the examination of clinical features of the cervical cancer patients classified into the development set and the validation set, stages, histologic grades, histologic types, tumor size of cervical cancer, smoker/non-smoker, and age of the cervical cancer patients were examined, and they were classified by the ISH method according to the human papillomavirus DNA integration patterns.

The patient group, in which the frequency of the episomal pattern observed in tumor tissues observed by the HPV ISH result accounted for 80% or higher was re-classified into group A, and the patient group, in which the multicopy tandem-repetition integrated pattern or the single-copy integration pattern was observed or a signal was not observed (postulated that a low copy number of integration which is experimentally undetectable was present), was re-classified into group B, and finally, the radiotherapy prognosis was observed by distinguishing the case when the episomal pattern was observed predominantly from the case when the integration pattern was observed predominantly.

Additionally, analyses were performed where there were any differences between the groups with or without an event, in terms of potential confounding factors, which are clinical features such as age, stages, histologic grades, etc., of cervical cancer, examined in Table 2.

The values of the area under the receiver operating characteristic curve (AUC) of the multivariable cox proportional hazards model obtained above were 0.77 (95% Confidence Interval; CI 0.66 to 0.87) for the development set, and 0.66 (95% CI 0.58 to 0.73) for the validation set.

As shown in Table 3, it was confirmed that the AUC value for the development set was 0.7706, and the value at 95% confidence interval was from 0.6758 to 0.8654; the AUC value for the validation set was 0.6558, and the value at 95% confidence interval was from 0.5843 to 0.7273, and the AUC value for the entire patient groups was 0.6993, and the value at 95% confidence interval was from 0.6403 to 0.7582. That is, it was confirmed that the reliability of the multivariable cox proportional hazards model obtained in the present invention from the human papillomavirus DNA integration patterns was high.

In the present invention, group B may have a hazard ratio of 1.4 to 7.44 when the hazard ratio regarding the survival rate of group A is set at 1, and preferably, group B may have a hazard ratio of 3.0 to 3.5.

As shown in Table 4, it was confirmed that the AUC value for the hazard ratios of the re-classified group A and the re-classified group B were obtained from the multivariable cox proportional hazards model, and it was confirmed that the hazard ratio increased to 7.68 in the development set, 2.43 in the validation set, and 3.23 in the entire data, when the hazard ratio was set at 1 in group A.

Additionally, in order to confirm whether the groups A and B re-classified in the present invention were appropriate criteria for determining the prognosis of cervical cancer patients, the hazard ratios were compared according to the stages and histologic grades of determining the real degree of progress and degree of hazard of cervical cancer using the multivariable cox proportional hazards model, and as a result, it was confirmed that the hazard ratios of the re-classified groups A and B, which were rated 'poor' in the diagnostic stages and histologic grades of cervical cancer, increased, as was the case of group B.

That is, it was confirmed that the hazard ratios were significantly lowered in the invasive cervical cancer patients, in which 80% or more of tumor cells were observed to have the HPV DNA with the episomal pattern, through the multivariable cox proportional hazards model developed in the present invention.

Figure 8:
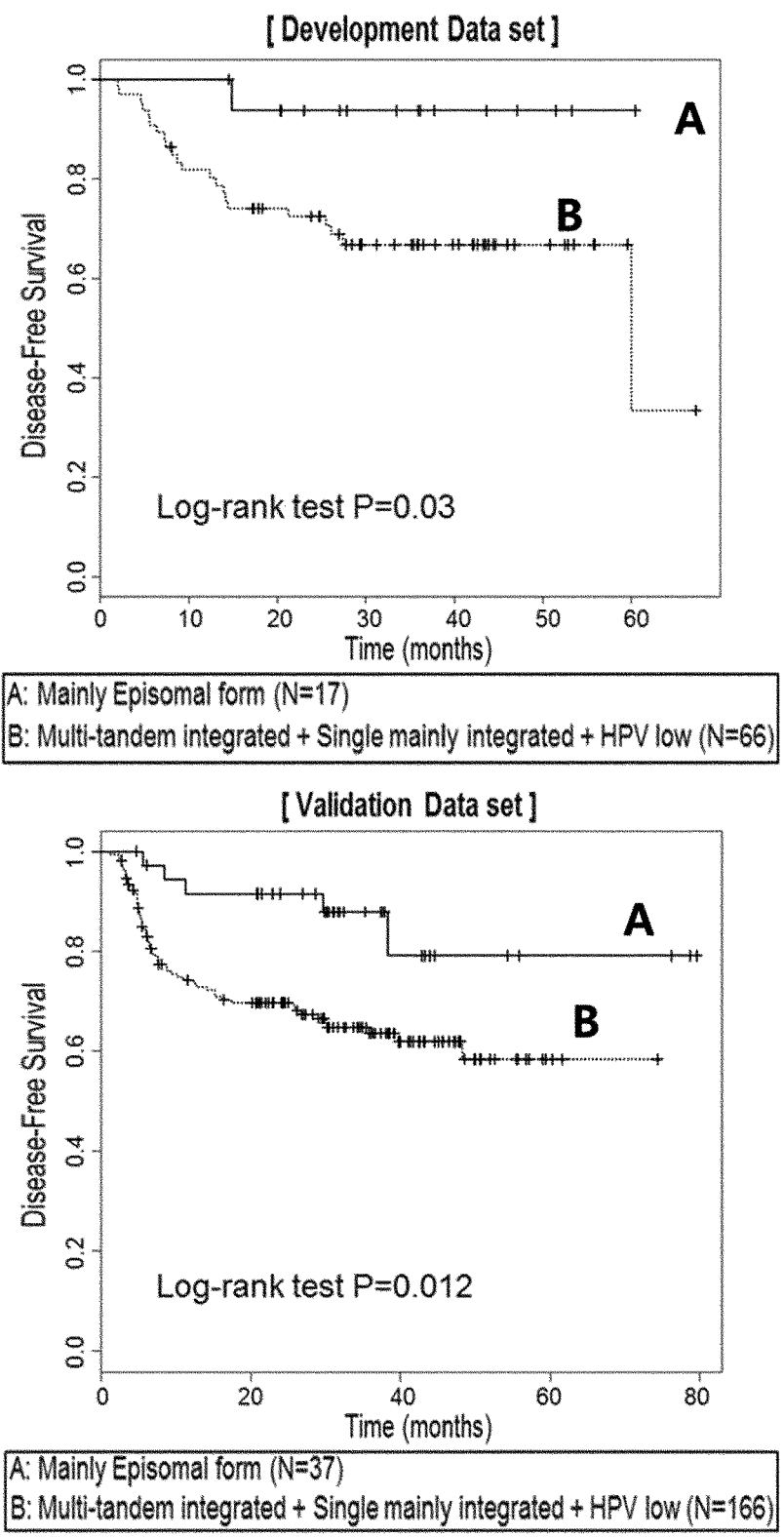
FIG. 8 shows the data illustrating the disease-free survival rate according to human papillomavirus DNA integration patterns in a development set and a validation set.

FIG. 8 shows the data illustrating the disease-free survival rate according to human papillomavirus DNA integration patterns in the development set and the validation set, in which group B was shown to have a lower disease-free survival rate than that of group A, and group A was shown to have 80% or higher of a disease-free survival rate even 80 months after radiotherapy.

In the present invention, for the analysis of the prognosis of cervical cancer, the patients were classified into a total of four risk groups (good-fairly good-fairly poor-poor) from the low risk group to the high risk group based on the prognostic indices from the multivariable cox proportional hazards model. The prognostic indices can be obtained from the linear predictor of the multivariable cox proportional hazards model, and it is a value obtained in a model by multiplying a regression coefficient to each variable by a value-based weighting, and adding them thereafter. The patients were classified into four groups on the basis of mean-std, mean, mean+std based on the mean and standard deviation (std) values of the prognostic indices obtained from the model.

The analyzed survival rate after two years' radiotherapy of the group with the lowest risk (good) may be from 90% to 95%, that of the second lowest risk group (fairly good) after radiotherapy for 2 years may be 80% to 85%, that of the second highest risk group (fairly poor) after radiotherapy for 2 years may be 70% to 75%, and that of the highest risk group (poor) after radiotherapy for 2 years may be 40% to 45%.

Figure 9:
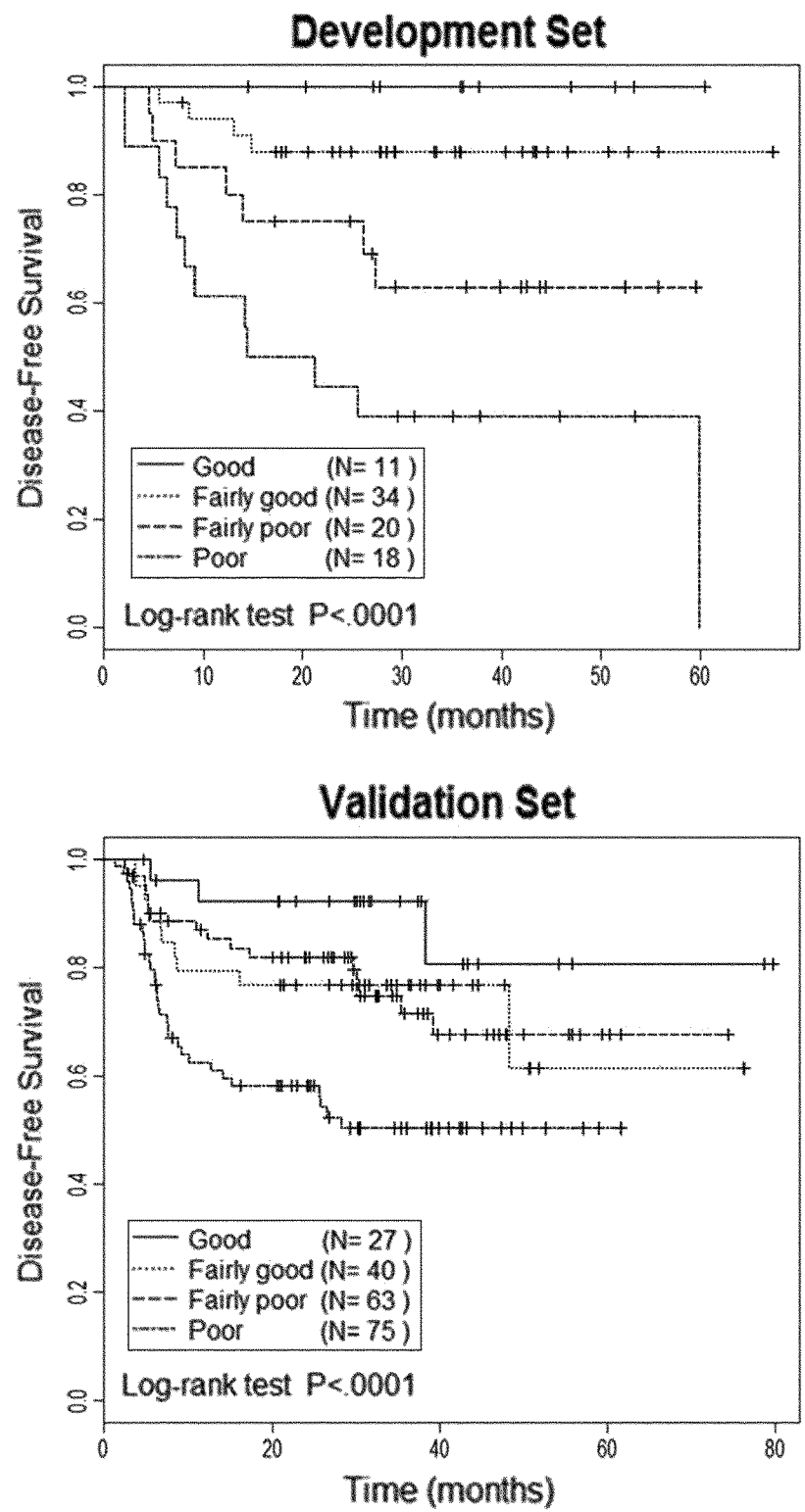
FIG. 9 shows the data illustrating the disease-free survival rate in a development set and a validation set, when classified into four risk groups from the most risky group to the least risky group according to the survival rate analyzed from the multivariable cox proportional hazards model.

In an exemplary embodiment of the present invention, patients were classified into two groups of a low risk group and a high risk group according to the risk probability analyzed based on the one year or two year survival rates after radiotherapy. As shown in FIG. 9, when the patients were classified into four groups according to the survival rates analyzed from the multivariable cox proportional hazards model, the disease-free survival rates in the development set and the validation set were shown.

FIGS. 10 and 11 show the data illustrating the hazard ratio (HR) of the disease-free survival rate of the four risk groups classified according to the survival rates analyzed in the development set and in the validation set, respectively, and the patient groups classified by the human papillomavirus DNA integration patterns that belong to the four risk groups. When the hazard ratio of the second lowest risk group (fairly good) was set at 1 because there was no event present in the lowest risk group (good), the hazard ratio of the second highest risk group (fairly poor) was 3.33 (95% CI: 0.97 to 11.40, P=0.0552), the hazard ratio of the highest risk group (poor) was 7.24 (95% CI: 2.32 to 22.57, P=0.0006), and in fact, the patients who were classified to the high risk group were shown to have high hazard ratios, and most of the patients belonging to the low risk group were the patients classified to group A, in which the human papillomavirus DNA was integrated in an episomal pattern.

Figure 12:
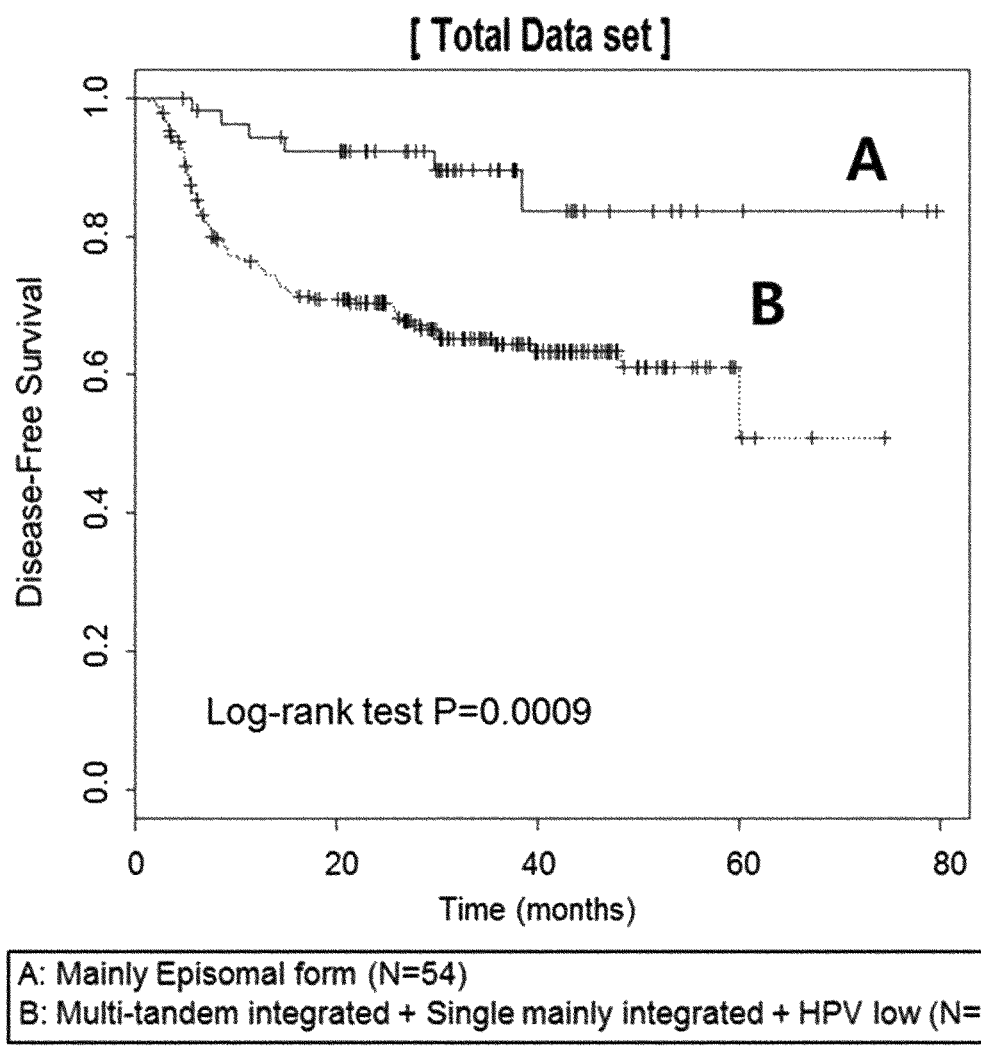
FIG. 12 shows the data illustrating the disease-free survival rate when the entire patient groups were classified into two groups according to the human papillomavirus DNA integration patterns.
Figure 13:
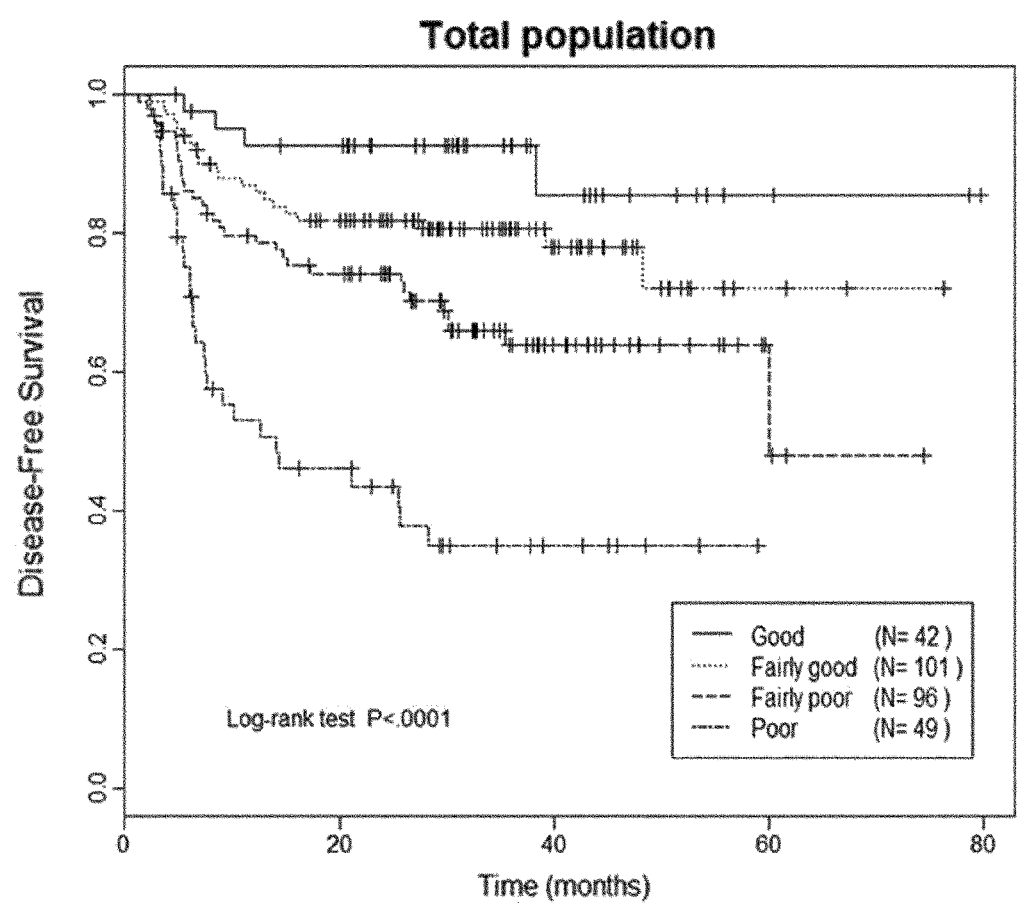
FIG. 13 shows the data illustrating the disease-free survival rate in total population when the entire patient groups were classified into four risk groups according to the survival rate analyzed from the multivariable cox proportional hazards model.

FIGS. 12 to 14 show the data analyzed with respect to the entire patient groups combining the development set and the validation set, and as shown in FIG. 12, it was confirmed that the survival rates of group A and group B classified according to the human papillomavirus DNA integration patterns of the entire patient groups showed survival rates similar to those representing each of the development set and the validation set, respectively.

Additionally, as shown in FIGS. 13 and 14, when the hazard ratios of the four risk groups classified according to the survival rates analyzed from the entire patient groups were examined, provided that the hazard ratio of the lowest risk group (good) was set at 1, the hazard ratio of the second lowest risk group (fairly good) was 2.33 (95% CI: 0.80 to 6.79, P=0.1209), the hazard ratio of the second highest risk group (fairly poor) was 4.06 (95% CI: 1.44 to 11.47, P=0.0083), and the hazard ratio of the highest risk group (poor) was 10.22 (95% CI: 3.58-29.15, P<0.0001), thus showing results similar to those of FIGS. 10 and 11, and most of the patients belonging to the low risk group were confirmed to be the patients classified to group A, in which the human papillomavirus DNA was integrated in an episomal pattern.

These statistically significant values can be very effectively used for determining the survival rate of patients with locally progressed cervical cancer, who received radiotherapy. Additionally, in the case when the cells having an episomal pattern and those having a pattern integrated into the chromosome of a host cell are mixed in tumor tissues, the frequencies accounted for can be digitized using the multivariable cox proportional hazards model, which was obtained by the analysis of the results using the ISH method, thereby accurately and precisely classifying the patient groups, thereby obtaining an appropriate cut-off point for determining treatment prognosis.

That is, the method of analyzing the prognosis of cervical cancer of the present invention includes more specifically: (a) obtaining tumor tissues from cervical cancer patients and observing their human papillomavirus DNA integration patterns using the in situ hybridization (ISH) method; (b) classifying the patient group with an episomal pattern or a group with a multicopy tandem-repetition integrated pattern or a single-copy integration pattern, where a signal is not observed, according to the human papillomavirus DNA integration patterns; and (c) analyzing the prognosis after radiotherapy according to the above classification.

Step (c) is characterized in that it can predict survival rates and hazard ratios using the multivariable cox proportional hazards model obtained to enable the prediction of the result of radiotherapy according to the human papillomavirus DNA integration patterns, and step (c) may be followed by further performing (d) analyzing the survival rates of the classified patient groups using the multivariable cox proportional hazards model and classifying them to a low risk group or a high risk group.

Additionally, classifying into a low risk group or a high risk group in step (d) may be classified into four risk groups (good-fairly good-fairly poor-poor) from the low risk group (good) to the high risk group (poor), according to the survival rates analyzed from the multivariable cox proportional hazards model.

Additionally, the present invention also provides a method of individualizing the cervical cancer treatment, which includes: classifying cervical cancer patients according to the human papillomavirus DNA integration patterns, and analyzing the prognosis thereof; and performing the use of an appropriate radiation and/or an anti-cancer agent according to the analysis.

As used herein, the term "individualization" refers to a method of treatment which is differentiated according to the characteristics of each patient and the analyzed prognosis thereof, instead of applying treatments to all the patients in the same manner. In the present invention, the prognosis of cervical cancer patients classified according to the human papillomavirus DNA integration patterns can be analyzed and the treatment method may vary depending on the results of analysis.

Specifically, the method of individualizing the cervical cancer treatment of the present invention may include (a) obtaining tumor tissues from cervical cancer patients and observing their human papillomavirus DNA integration patterns using in situ hybridization (ISH) method; (b) classifying the cervical cancer patients according to the human papillomavirus DNA integration patterns; and (c) performing the use of an appropriate radiation and/or an anti-cancer agent according to the classification.

A method of analyzing the prognosis of cervical cancer of the present invention may include a method of monitoring the cervical cancer treatment, which includes: classifying cervical cancer patients according to the human papillomavirus DNA integration patterns, and analyzing the prognosis thereof; and performing the use of an appropriate radiation and/or an anti-cancer agent according to the analysis.

That is, when the HPV DNA integration patterns were classified by the method of analyzing the prognosis of cervical cancer of the present invention, the prognosis of the cervical cancer patients having tumors with an episomal pattern and an integrated pattern can be apparently distinguished, and thus the survival rate of cervical cancer patients, in particular invasive cervical cancer patients, after radiotherapy can be more accurately analyzed. Additionally, since the cervical cancer patients having tumors with an episomal pattern have a prognosis with a low recurrent risk after radiotherapy, they can minimize the use of radiotherapy or anticancer agents thereby maintaining reducing complications due to treatments while maintaining the complete cure rate. For the cervical cancer patients having tumors with an integrated pattern, their complete cure rate can be improved by applying a treatment method which can increase complete cure rate while improving the quality of their lives.

The steps of the method for analyzing the prognosis of cervical cancer described above may be embodied using software programs capable of performing these steps, and in this case, the programs may be stored in a computer-readable medium or may be transmitted by a transmission medium or a computer data signal connected to a carrier wave.

Specifically, the present invention includes as the computer-readable medium, in which the computer executable instructions for analyzing the prognosis of cervical cancer are contained thereon, a computer-readable medium which includes: a code for confirming the human papillomavirus DNA integration patterns observed in tumor tissues of cervical cancer patients using the in situ hybridization (ISH) method; and a code for analyzing the prognosis of cervical cancer according to the human papillomavirus DNA integration patterns.

Regarding the computer-readable medium of the present invention, the human papillomavirus DNA integration patterns may be classified into group 1, which includes an episomal form; group 2, which has a single-copy integration pattern without including an episomal form; group 3, which has a multicopy tandem-repetition integrated pattern; and group 4, in which the human papillomavirus DNA integration pattern is not observed.

Regarding the computer-readable medium of the present invention, the cervical cancer patients may be classified according to the human papillomavirus DNA integration pattern into: group A, in which the frequency of an episome pattern appears in a range of 80% to 100% of the patients; group B, in which the single-copy integration pattern or the multicopy tandem-repetition integrated pattern are observed, or the human papillomavirus DNA integration pattern is not observed in the patients, and group B may have a hazard ratio of 1.4 to 7.44 when the hazard ratio regarding the survival rate of group A is set at 1.

Regarding the computer-readable medium of the present invention, the hazard ratio may be measured using the multivariable cox proportional hazards model obtained so that the result of radiotherapy according to the human papillomavirus DNA integration patterns can be analyzed.

The computer-readable medium is a medium for storing information, which is commercially available for purchase or can be accessed to a computer using custom-made interface. Examples of representative computer-readable media may include memories (e.g., RAM, ROM, flash memories, etc.), optical storage media (e.g., CD-ROM), magnetic storage media (e.g., computer hard drives, floppy discs, etc.), punch cards, or other commercially available media. Information may be delivered between a system of interest and a medium, between computers, or between a computer and a computer-readable medium for storage or for access to the stored information. These transmission may be performed electrically or other usable methods such as IR link, wireless connection, etc.

As can be understood by those skilled in the art to which the present invention belongs, the methods described herein is a computer executable instruction, and may be embodied partially or in its entirety on a known computer-readable medium. For example, the methods described herein may be embodied in hardware.

Alternatively, for example, the methods of the present invention can be stored in at least one memory or other computer-readable medium, and can be embodied into a software embodied in at least one processor. As already known, a processor may be connected to one or more of controllers, a calculation unit, and/or other unit of a computer system, or may be transplanted into a desirable firmware. When the processor is transplanted into a software, routine, as is already known, can be stored in a computer-readable memory such as RAM, ROM, flash memories, magnetic discs, laser discs, or other storing media. Likewise, the software may be delivered to a computer device in a telecommunication channel, such as a telephone line, internet, wireless access, or by a known delivery method, including a transportable medium, such as a computer-readable disc, a flash drive, etc.

More generally, as can be understood by those skilled in the art to which the present invention belongs, the various steps described previously may be embodied into a method that can be embodied in various blocks, operations, tools, modules, and hardware, firmware, software, or in a combination of hardware, firmware, and/or software. When it is embodied in hardware, a part or entirety of the blocks, operations, or techniques, etc., may be embodied in custom IC, application specific integrated circuit (ASIC), field programmable logic array (FPGA), and programmable logic array (PLA).

When it is embodied in software, the software may be stored in a known computer-readable medium such as a magnetic disc, an optical disc, or other storage medium, computer RAM, ROM, or flash memory, a processor, a hard disc drive, an optical disc drive, a tape drive, etc. Likewise, the software may be delivered by a known delivery method including, for example, a computer-readable disc or other portable computer storage mechanism to a user or a computer system.

The steps of the claimed methods may be operated in a plurality of other general purpose or specific purpose computing system environment or structures. Examples of the known computing systems, environment, and/or structures suitable for use with the claimed method or system may include personal computers, server computers, portable or laptop devices, multiprocessor systems, microprocessor-based systems, set-top boxes, programmable consumer electronics, network PCs, minicomputers, mainframe computers, distributed computing environment including the systems or devices described above, etc., but are not limited thereto.

The steps of the claimed methods may be explained in general background of computer-executable instructions, such as program modules which are executed by computers. In general, program modules include routines, programs, objects, components, data structures, etc., which can execute particular tasks or particular abstract data types. The methods of the present invention may be also executed in a distributed computing environment, in which operations are executed by remote controlling devices connected by communication network. In both of the integrated computing environment and distributed computing environment, the program modules may be positioned in a local and remote computer storage medium, including memory storage devices.

The present invention will be explained in more details so that those skilled in the art to which the present invention belongs can easily practice, with reference to the accompanying preferred Examples. However, the present invention can be embodied in various other forms and should not be limited to those disclosed herein.

EXAMPLES

Example 1

Observation of Integration Form of Human Papillomavirus DNA by in Situ Hybridization Method In the present invention, for the observation of the human papillomavirus DNA integration patterns by in situ hybridization ("ISH", hereinafter) method, the tumor tissues obtained from 80 cervical cancer patients who received curative radiotherapy with or without in combination with a chemotherapy in the National Cancer Center (Korea) were observed.

First, the isolated tissues were prepared into samples of formalin-fixed, paraffin-embedded (FFPE) blocks, sliced into a size of 3 μm thickness and attached onto a slide-glass coated with fresh silane III.

Then, the samples with an episomal pattern and those with an integration pattern were detected using a commercially available HPV ISH system (Ventana Inform HPV, Tucson, Ariz., USA). To be brief, the detection of high risk HPV ISH was performed using BenchMark™, automated slide staining system (Ventana Medical Systems), iView Blue Plus Detection Kit, which employs an antibody detection method, in which alkaline-phosphatase are conjugated to antibodies, and INFORM® HPV III 16 Family probes (Ventana-Roche), according to a recommended manual.

HPV III ISH Family 16 probe set includes a HPV genomic probe cocktail in a formamide-based diluent, and the probe cocktail has an affinity for the following high risk HPV genotypes; 16, 18, 31, 33, 35, 39, 45, 51, 52, 56, 58, 및 66.

The hybridization signal was indicated by Tetrazole Blue and nuclear fast red (NFR) counter staining, and the stained form of the cervical cancer tissues were observed using a microscope. According to the manual, a spot (such as distinct dots) signal is regarded as an integrated pattern, and the Navy-Blue staining over the entire nuclei is evaluated as an episome pattern.

FIGS. 3 to 6 show pictures observed according to the in situ hybridization (ISH) method, and group 1, which has the single-copy integration pattern having an episomal form, was confirmed to be darkly stained throughout the entire nuclei of cells (FIG. 3). Group 2, which shows a feature illustrating the presence of one or several millet-like small dots within a nucleus, or it was vaguely observed, and it was more accurately distinguished under a microscope (400× magnification) (FIG. 4). Group 3, which has a multicopy tandem-repetition integrated pattern, was observed to have dots with a big size, which were easily confirmed even under a microscope (100× magnification) (FIG. 5). Group 4 was confirmed that there was no human papillomavirus DNA integration pattern observed (FIG. 6).

Example 2

Observation of Integration Form of Human Papillomavirus DNA by PCR Method

In the present invention, the integration pattern of the human papillomavirus DNA was observed in the tumor tissues of 80 cervical cancer patients of Example 1, in the same manner as in the previous study (Shin, H. J. et al., *PLoS One*, 9:e78995, 2014).

The DNA extraction, DNA amplification, and genotyping were performed in the same manner as reported previously (Kim J Y et al., *J Clin Oncol.*, 27:5088, 2009), and the real-time PCR was performed using ABI Prism 7900HT System and TaqMan Universal PCR Master Mix (PE Applied Biosystems, Perkin-Elmer, Foster City, Calif.).

Primers and probes were designed so that E2 hinge regions and E6 gene (Peitsaro P et al., *J Clin Microbiol.*, 40:886, 2002.), which are known to be most frequently destroyed during the progress of virus integration, can be specifically amplified (Table 1), and synthesized by Applied Biosystems® Life technologies (ABI).

TABLE 1

Primers and probes for the amplification of human papillomavirus DNA

| Name | | Sequence (5' -> 3') | SEQ ID NO |
|---|---|---|---|
| HPV 16-E2 | Forward primer | AAC GAA GTA TCC TCT CCT GAA ATT ATT AG | 1 |
| HPV 16-E2 | Reverse primer | CCA AGG CGA CGG CTT TG | 2 |
| HPV 16-E2 | Probe | VIC-5'-CAC CCC GCC GCG ACC CAT A-3'-MGB/NFQ | 3 |
| HPV 16-E6 | Forward primer | ACC GGT CGA TGT ATG TCT TGT TG | 4 |
| HPV 16-E6 | Reverse primer | GAT CAG TTG TCT CTG GTT GCA AAT C | 5 |

TABLE 1-continued

Primers and probes for the amplification of human papillomavirus DNA

| Name | | Sequence (5' -> 3') | SEQ ID NO |
|---|---|---|---|
| HPV 16-E6 | Probe | FAM-5'-TGC ATG GAG ATA CAC CTA CAT TGC ATG AAT ATA-3'-TAMRA | 6 |
| HPV 18-E2 | Forward primer | GGT GGT GCC AGC CTA TAA CAT T | 7 |
| HPV 18-E2 | Reverse primer | CCA TAG TTC CTC GCA TGT GTC TT | 8 |
| HPV 18-E2 | Probe | VIC-5'-AAA AGT AAA GCA CAT AAA GCT ATT GAA CTG CAA ATG GC-3'-MGB/NFQ | 9 |
| HPV 18-E6 | Forward primer | AAT ACT ATG CGC GCT TTT GAG | 10 |
| HPV 18-E6 | Reverse primer | TTC AAA TAC CTC TGT AAG TTC CAA TAC TG | 11 |
| HPV 18-E6 | Probe | FAM-5'-TAC AAG CTA CCT GAT CTG TGC ACG GAA CTG-3'-TAMRA | 12 |
| HPV 58-E2 | Forward primer | GAG GCC ACC AAC AAC GAA AG | 13 |
| HPV 58-E2 | Reverse primer | GTC CAC GGC GCA GTC TGT ATA | 14 |
| HPV 58-E2 | Probe | VIC-5'-AAG CGA CGA CGA CTC GAT TTA CCA GAC TC-3'-MGB/NFQ | 15 |
| HPV 58-E6 | Forward primer | TGA CAG CTC AGA CGA GGA TGA A | 16 |
| HPV 58-E6 | Reverse primer | CAC AAG TGT AAC AAC AAG TTA CAA TGT AGT | 17 |
| HPV 58-E6 | Probe | FAM-5'-ACA AGA ACA ACC GGC CAC AGC TAA TT-3'-TAMRA | 18 |

(In the above probes, VIC and FAM indicate reporter dyes, and MGB/NFG and TAMRA indicate Quencher dyes.)

DNA of each sample isolated from each tumor tissue in an amount of 50 ng was used for each reaction, and the standard curve was prepared by amplifying the continuously diluted product of $10^3$ to $10^6$ copies of HPV clones of pBR322 vector. Additionally, three control groups not containing the template DNA were included in each reaction, and all the experiments were performed in three sets.

As shown in FIG. 7A, when 80 cervical cancer patients were classified to each group according to the human papillomavirus DNA integration patterns as a result of qPCR, it was confirmed that groups 1 to 4 were shown to have a ratio of 25%, 25%, 34%, and 12%, respectively.

Example 3

Analysis of Human Papillomavirus DNA Integration Patterns According to ISH Method and qPCR Method In order to compare the accuracy of the human papillomavirus DNA integration patterns according to the ISH method and the qPCR method, the groups of human papillomavirus DNA integration patterns classified according to the result observed by the ISH method of Example 1 and the groups of human papillomavirus DNA integration patterns classified according to the result observed by the qPCR method of Example 2 were compared.

As a result, as shown in FIG. 7B, it was confirmed that there was a big difference between the PCR method and the ISH method. In particular, when the patient group corresponding to group 1 classified by the PCR method was re-classified by the ISH method, it was confirmed that group 1 had 48%, group 2 had 9%, and group 3 had 43%, whereas the patient group corresponding to group 3 classified by the PCR method was re-classified by the ISH method, it was confirmed that group 1 had 23%, group 2 had 4%, and group 3 had 73%.

That is, in the patient group classified to group 1 by the PCR result, as many as 43% of patients that belonged to group 3 by the ISH result, whereas in the patient group classified to group 3 by the PCR result, as many as 23% of patients that belonged to group 1 by the ISH result, thus suggesting that the PCR result alone was not able to provide an accurate distinction between the tumor group with an episomal pattern (group 1) and the tumor group with a multicopy tandem-repetition integrated pattern (group 3).

Example 4

Establishment of a Model Capable of Analyzing the Prognosis of Cervical Cancer Patients In order to establish a model capable of analyzing the prognosis of cervical cancer patients based on the result of the ISH experiment analyzing the human papillomavirus DNA integration patterns, the tumor tissues were obtained from 288 constitute cervical cancer patients who received curative radiotherapy chemotherapy with or without in combination with chemotherapy in the National Cancer Center (Korea), and among them, the samples from 83 patients were used as a development set for the establishment of a model and those from 205 patients were used as a validation set, and the human papillomavirus DNA integration patterns were analyzed in the same manner as in Example 1.

Then, according to the human papillomavirus DNA integration patterns, the patient group, in which the frequency of an episome pattern appeared in a range of 80% to 100% of the patients was classified into group A; and the patient group, in which the single-copy integration pattern or the multicopy tandem-repetition integrated pattern were observed, or the human papillomavirus DNA integration pattern was not observed in the patients was classified into group B.

TABLE 2

| Characteristics | Subgroup | Development data (Set 1) (N = 83) | | | | Validation data (Set 2 + 3 + 4) (N = 205) | |
|---|---|---|---|---|---|---|---|
| | | Total (N = 83) | No Event (%) (N = 60) | Event (%) (N = 23) | p-value | Total (N = 288) | No Event (%) (N = 142) |
| Group by Integration pattern | | | | | | | |
| Cut = 80% | A* | 17 | 16 (94.12) | 1 (5.88) | 0.0316 | 37 | 32 (86.49) |
| | B* | 66 | 44 (66.67) | 22 (33.33) | | 168 | 110 (65.48) |
| Stage group | | | | | | | |
| | ~IIB | 68 | 54 (79.41) | 14 (20.59) | 0.0039 | 155 | 117 (75.48) |
| | III/IVA/IVB | 15 | 6 (40) | 9 (60) | | 50 | 25 (50) |
| Histologic Grade | | | | | | | |
| | well/moderate | 73 | 56 (76.71) | 17 (23.29) | 0.0241 | 140 | 100 (71.73) |
| | poor | 10 | 4 (40) | 6 (60) | | 65 | 42 (64.62) |
| Histologic type | | | | | | | |
| | SCC | 79 | 60 (75.95) | 19 (24.05) | 0.0048 | 178 | 129 (72.47) |
| | AD/ASC | 4 | 0 (0) | 4 (100) | | 27 | 13 (48.15) |
| Tumor size | | | | | | | |
| | <4 cm | 41 | 34 (82.93) | 7 (17.07) | 0.0324 | 75 | 58 (77.33) |
| | ≥4 cm | 42 | 26 (61.9) | 16 (38.1) | | 130 | 84 (64.62) |
| Smoking | | | | | | | |
| | non-smoker | 67 | 51 (76.12) | 16 (23.88) | 0.1283 | 163 | 112 (68.71) |
| | present/ex-smoker | 16 | 9 (56.25) | 7 (43.75) | | 42 | 30 (71.43) |
| Age: | | 83 | 58.48 ± 13.41 | 52 ± 14.05 | 0.0551 | 205 | 55.57 ± 14.49 |

TABLE 2-continued

| Character-istics | Sub-group | Validation data (Set 2 + 3 + 4) (N = 205) | | | Total data (Set 1 + 2 + 3 + 4) (N = 288) | | | |
|---|---|---|---|---|---|---|---|---|
| | | Event (%) (N = 63) | p-value | Total (N = 288) | No Event (%) (N = 202) | Event (%) (N = 86) | p-value |
| Group by Integration pattern | | | | | | | |
| Cut = 80% | A* | 5 (13.51) | 0.0122 | 54 | 48 (88.89) | 6 (11.11) | 0.0008 |
| | B* | 58 (34.52) | | 234 | 154 (65.81) | 80 (34.19) | |
| Stage group | | | | | | | |
| | ~IIB | 38 (24.52) | 0.0007 | 223 | 171 (76.68) | 52 (23.32) | <.0001 |
| | III/IVA/IVB | 25 (50) | | 65 | 31 (47.69) | 34 (52.31) | |
| Histologic Grade | | | | | | | |
| | well/moderate | 40 (28.57) | 0.3252 | 213 | 156 (73.24) | 57 (26.76) | 0.0527 |
| | poor | 23 (35.38) | | 75 | 46 (61.33) | 29 (38.67) | |
| Histologic type | | | | | | | |
| | SCC | 49 (27.53) | 0.0107 | 257 | 189 (73.54) | 68 (26.46) | 0.0003 |
| | AD/ASC | 14 (51.85) | | 31 | 13 (41.94) | 18 (58.06) | |
| Tumor size | | | | | | | |
| | <4 cm | 17 (22.67) | 0.0573 | 116 | 92 (79.31) | 24 (20.69) | 0.0052 |
| | ≥4 cm | 46 (35.38) | | 172 | 110 (63.95) | 62 (36.05) | |
| Smoking | | | | | | | |
| | non-smoker | 51 (31.29) | 0.7336 | 230 | 163 (70.87) | 67 (29.13) | 0.5895 |
| | present/ex-smoker | 12 (28.57) | | 58 | 39 (67.24) | 19 (32.76) | |
| Age: | | 50.6 ± 14.39 | 0.0243 | 288 | 56.44 ± 14.21 | 50.98 ± 14.23 | 0.0031 |

A*: Mainly Episomal
B*: Multi-tandem integration + Single mainly Integrated + low HPV DNA As shown in Table 2, for the examination of clinical features of the cervical cancer patients classified into the development set and the validation set, stages, the cervical cancer patients were examined regarding the stages, histologic grades, histologic types, tumor size of cervical cancer, smoker/non-smoker, and age. Then, it was analyzed whether there was a difference between the groups with and without an event, regarding the potential confounding factors, i.e., clinical features of the cervical cancer patients, such as age of the cervical cancer patients, stages and histologic grades of their cervical cancer, examined in Table 2.

TABLE 3

| Model | AUC | 95% CI |
|---|---|---|
| Development set | 0.7706 | (0.6758-0.8654) |
| Validation set | 0.6558 | (0.5843-0.7273) |
| Total set | 0.6993 | (0.6403-0.7582) |

As shown in Table 3, it was confirmed that the value of the area under the receiver operating characteristic curve (AUC) for the development set was 0.7706, and the value at 95% confidence interval (CI) was from 0.6758 to 0.8654; the AUC value for the validation set was 0.6558, and the value at 95% confidence interval was from 0.5843 to 0.7273, and the AUC value for the entire patient groups was 0.6993, and the value at 95% confidence interval was from 0.6403 to 0.7582. That is, it was confirmed that the reliability of the multivariable cox proportional hazards model obtained in the present invention from the human papillomavirus DNA integration patterns was high.

Example 5

Measurement of Survival Rates and Hazard Ratios Using a Multivariable Cox Proportional Hazards Model In the present invention, a multivariable cox proportional hazards model was established based on the data of Example 4 using a known method in order to obtain the multivariable cox proportional hazards model according to the human papillomavirus DNA integration patterns, and the survival rates of group A and group B classified according to the human papillomavirus DNA integration patterns from the multivariable cox proportional hazards model obtained above, and the hazard ratios on the survival rates were measured.

As shown in FIG. 8, group B was shown to have a lower disease-free survival rate than group A, and the patients in group A were shown to have a survival rate of 80% or higher even after 80 months of radiotherapy.

TABLE 4

| Characteristics | Development data (set 1) Multivariable Select 0.1 ER (95% CI) N = 83 | p-value Event = 23 | Validation data (set 2 + 3 + 4) Developmental model Select HR (95% CI) N = 205 | p-value Event = 63 | Total data (set 1 + 2 + 3 + 4) Developmental model Select HR (95% CI) N = 288 | p-value Event = 86 |
|---|---|---|---|---|---|---|
| Group by Integration pattern | | | | | | |
| cut = 80% A* | 1 | | 1 | | 1 | |
| B* | 7.68 (1.03-57.22) | 0.0466 | 2.43 (0.97-6.11) | 0.0596 | 3.23 (1.4-7.44) | 0.0058 |
| Stage group | | | | | | |
| ~IIB | 1 | | 1 | | 1 | |
| III/IVA/IVB | 4.57 (1.75-11.97) | 0.002 | 3.21 (1.9-5.41) | <0001 | 3.26 (2.1-5.07) | <0001 |
| Histologic Grade | | | | | | |
| well/moderate | 1 | | 1 | | 1 | |
| poor | 7.04 (2.24-22.14) | 0.0008 | 1.22 (0.73-2.05) | 0.4437 | 1.58 (1.01-2.47) | 0.0468 |
| Age: | 0.97 (0.93-1.00) | 0.045 | 0.98 (0.96-1.00) | 0.0118 | 0.98 (0.96-0.99) | 0.0029 |

A*: Mainly Episomal form
B*: Multi-tandem integration + Single mainly integrated + HPV low As shown in Table 4, it was confirmed that the hazard ratio of group B was 7.68 (95% CI: 1.03-57.22, P=0.047), showing an increase of the degree of hazard, when the hazard ratio of group A was set at 1, in the development set.

In order to confirm whether the groups A and B re-classified in the present invention were appropriate criteria for determining the prognosis of cervical cancer patients, the hazard ratios were compared according to the stages and histologic grades of determining the real degree of progress (the variables indicated as stage group in the Table 4) and degree of hazard (histologic grades in the Table 4) of cervical cancer using the multivariable cox proportional hazards model, and as a result, it was confirmed that the hazard ratios of the re-classified groups A and B, which were rated 'poor' in the diagnostic stages and histologic grades of cervical cancer, increased, as was the case of group B.

That is, it was confirmed that the hazard ratios were significantly lowered in the invasive cervical cancer patients, in which 80% or more of tumor cells were observed to have the HPV DNA with the episomal pattern, through the multivariable cox proportional hazards model developed in the present invention.

Example 6

Separation of Risk Groups According to the Survival Rates Analyzed from the Multivariable Cox Proportional Hazards Model In the present invention, the patient groups, the patients were divided four risk groups from the low risk group to the high risk group according to the survival rates analyzed from the multivariable cox proportional hazards model in Example 5.

To be brief, the patients were classified into four groups from a low risk group to a high risk group according to the risk probability analyzed based on the one year or two year survival rates after radiotherapy. As shown in FIG. 9, when the patients were classified into four groups according to the survival rates analyzed from the multivariable cox proportional hazards model, the disease-free survival rates in the development set and the validation set were shown.

As shown in FIGS. 10 and 11, the patient groups, which were divided into the four risk groups according to the survival rates analyzed in the development set and in the validation set and classified by the hazard ratio (HR) of the disease-free survival rate and the human papillomavirus DNA integration patterns that belong to the four risk groups, were analyzed. As a result, when the hazard ratio of the second lowest risk group (fairly good) was set at 1 because there was no event present in the lowest risk group (good), the hazard ratio of the second highest risk group (fairly poor) was 3.33 (95% CI: 0.97 to 11.40, P=0.0552), the hazard ratio of the highest risk group (poor) was 7.24 (95% CI: 2.32 to 22.57, P=0.0006), and in fact, the patients who were classified to the high risk group were shown to have high hazard ratios, and most of the patients belonging to the low risk group were the patients classified to group A, in which the human papillomavirus DNA was integrated in an episomal pattern.

Additionally, when the entire patient groups combining the development set and the validation set were analyzed by the method described above, it was confirmed, as shown in FIG. 12, that the survival rates of group A and group B classified according to the human papillomavirus DNA integration patterns of the entire patient groups showed survival rates similar to those representing each of the development set and the validation set of FIG. 8, respectively.

Additionally, as shown in FIGS. 13 and 14, when the hazard ratios of the four risk groups were examined, provided that the hazard ratio of the lowest risk group (good) was set at 1, the hazard ratio of the second lowest risk group (fairly good) was 2.33 (95% CI: 0.80 to 6.79, P=0.1209), the hazard ratio of the second highest risk group (fairly poor) was 4.06 (95% CI: 1.44 to 11.47, P=0.0083), and the hazard ratio of the highest risk group (poor) was 10.22 (95% CI: 3.58 to 29.15, P<0.0001), thus showing results similar to those of FIGS. 10 and 11, and most of the patients belonging to the low risk group were confirmed to be the patients classified to group A, in which the human papillomavirus DNA was integrated in an episomal pattern.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method for predicting the prognosis of and treating a patient with locally advanced cervical cancer within stage IB to stage IVB who received radiotherapy, the method comprising the steps of:
(A) classifying the patient into group A or group B,
(B) predicting the prognosis of cervical cancer, wherein the patient classified into group A has a good prognosis, and wherein group B has a hazard ratio of 1.4 to 7.44 when the hazard ratio regarding the survival rate of group A is set at 1, wherein the hazard ratio is measured using a multivariable cox proportional hazards model, and
(C) administering radiation and/or an anti-cancer agent to the patient, wherein the level of radiation and/or anti-cancer agent administered to the patient is reduced if the patient is classified into group A relative to the level to be administered if the patient is classified into group B;

wherein the step (A) comprises:
(I) obtaining a cervical tumor tissue from the patient with locally advanced cervical cancer within stage IB to stage IVB who received radiotherapy, wherein the cervical tumor tissue contains tumor cells and wherein the tumor cells are cells in the tumor tissue that contain human papillomavirus (HPV) DNA,
(II) determining the HPV DNA pattern in tumor cells of the tumor tissue by in situ hybridization (ISH),
(III) determining the percentage of the tumor cells with an episome pattern in the tumor tissue, (IV) classifying the patient into group A if the tumor tissue has an episome pattern in 80% to 100% of the tumor cells, and
(V) classifying the patient into group B if the tumor tissue does not have an episome pattern in 80% to 100% of the tumor cells.

2. The method of claim 1, wherein the hazard ratio is measured by using a multivariable cox proportional hazards model derived such that results of radiotherapy according to the human papillomavirus DNA patterns are analyzable.

3. The method of claim 1, wherein the cervical cancer is invasive cervical cancer.

* * * * *

SEQUENCE LISTING

<160> NUMBER OF SEQ ID NOS: 18

<210> SEQ ID NO 1
<211> LENGTH: 29
<212> TYPE: DNA
<213> ORGANISM: Artificial
<220> FEATURE:
<223> OTHER INFORMATION: HPV 16-E2 Forward Primer

<400> SEQUENCE: 1
aacgaagtat cctctcctga aattattag                               29

<210> SEQ ID NO 2
<211> LENGTH: 17
<212> TYPE: DNA
<213> ORGANISM: Artificial
<220> FEATURE:
<223> OTHER INFORMATION: HPV 16-E2 Reverse primer

<400> SEQUENCE: 2
ccaaggcgac ggctttg                                            17

<210> SEQ ID NO 3
<211> LENGTH: 19
<212> TYPE: DNA
<213> ORGANISM: Artificial
<220> FEATURE:
<223> OTHER INFORMATION: HPV 16-E2 Probe

<400> SEQUENCE: 3
caccccgccg cgacccata                                          19

<210> SEQ ID NO 4
<211> LENGTH: 23
<212> TYPE: DNA
<213> ORGANISM: Artificial
<220> FEATURE:
<223> OTHER INFORMATION: HPV 16-E6 Forward primer

<400> SEQUENCE: 4
accggtcgat gtatgtcttg ttg                                     23

<210> SEQ ID NO 5
<211> LENGTH: 25
<212> TYPE: DNA
<213> ORGANISM: Artificial
<220> FEATURE:
<223> OTHER INFORMATION: HPV 16-E6 Reverse primer

<400> SEQUENCE: 5
gatcagttgt ctctggttgc aaatc                                   25

<210> SEQ ID NO 6
<211> LENGTH: 33
<212> TYPE: DNA
<213> ORGANISM: Artificial
<220> FEATURE:
<223> OTHER INFORMATION: HPV 16-E6 Probe

<400> SEQUENCE: 6
tgcatggaga tacacctaca ttgcatgaat ata                          33

<210> SEQ ID NO 7
<211> LENGTH: 22
<212> TYPE: DNA
<213> ORGANISM: Artificial

```
<220> FEATURE:
<223> OTHER INFORMATION: HPV 18-E2 Forward primer

<400> SEQUENCE: 7
ggtggtgcca gcctataaca tt                                         22

<210> SEQ ID NO 8
<211> LENGTH: 23
<212> TYPE: DNA
<213> ORGANISM: Artificial
<220> FEATURE:
<223> OTHER INFORMATION: HPV 18-E2 Reverse primer

<400> SEQUENCE: 8
ccatagttcc tcgcatgtgt ctt                                        23

<210> SEQ ID NO 9
<211> LENGTH: 38
<212> TYPE: DNA
<213> ORGANISM: Artificial
<220> FEATURE:
<223> OTHER INFORMATION: HPV 18-E2 Probe

<400> SEQUENCE: 9
aaaagtaaag cacataaagc tattgaactg caaatggc                        38

<210> SEQ ID NO 10
<211> LENGTH: 21
<212> TYPE: DNA
<213> ORGANISM: Artificial
<220> FEATURE:
<223> OTHER INFORMATION: HPV 18-E6 Forward primer

<400> SEQUENCE: 10
aatactatgg cgcgctttga g                                          21

<210> SEQ ID NO 11
<211> LENGTH: 29
<212> TYPE: DNA
<213> ORGANISM: Artificial
<220> FEATURE:
<223> OTHER INFORMATION: HPV 18-E6 Reverse primer

<400> SEQUENCE: 11
ttcaaatacc tctgtaagtt ccaatactg                                  29

<210> SEQ ID NO 12
<211> LENGTH: 30
<212> TYPE: DNA
<213> ORGANISM: Artificial
<220> FEATURE:
<223> OTHER INFORMATION: HPV 18-E6 Probe

<400> SEQUENCE: 12
tacaagctac ctgatctgtg cacggaactg                                 30

<210> SEQ ID NO 13
<211> LENGTH: 20
<212> TYPE: DNA
<213> ORGANISM: Artificial
<220> FEATURE:
<223> OTHER INFORMATION: HPV 58-E2 Forward primer

<400> SEQUENCE: 13
gaggccacca acaacgaaag                                            20
```

```
<210> SEQ ID NO 14
<211> LENGTH: 21
<212> TYPE: DNA
<213> ORGANISM: Artificial
<220> FEATURE:
<223> OTHER INFORMATION: HPV 58-E2 Reverse primer

<400> SEQUENCE: 14
gtccacggcg cagtctgtat a                                              21

<210> SEQ ID NO 15
<211> LENGTH: 29
<212> TYPE: DNA
<213> ORGANISM: Artificial
<220> FEATURE:
<223> OTHER INFORMATION: HPV 58-E2 Probe

<400> SEQUENCE: 15
aagcgacgac gactcgattt accagactc                                      29

<210> SEQ ID NO 16
<211> LENGTH: 22
<212> TYPE: DNA
<213> ORGANISM: Artificial
<220> FEATURE:
<223> OTHER INFORMATION: HPV 58-E6 Forward primer

<400> SEQUENCE: 16
tgacagctca gacgaggatg aa                                             22

<210> SEQ ID NO 17
<211> LENGTH: 30
<212> TYPE: DNA
<213> ORGANISM: Artificial
<220> FEATURE:
<223> OTHER INFORMATION: HPV 58-E6 Reverse primer

<400> SEQUENCE: 17
cacaagtgta acaacaagtt acaatgtagt                                     30

<210> SEQ ID NO 18
<211> LENGTH: 26
<212> TYPE: DNA
<213> ORGANISM: Artificial
<220> FEATURE:
<223> OTHER INFORMATION: HPV 58-E6 Probe

<400> SEQUENCE: 18
acaagaacaa ccggccacag ctaatt                                         26
```